US006562214B1

United States Patent
Amrhein et al.

(10) Patent No.: US 6,562,214 B1
(45) Date of Patent: May 13, 2003

(54) LAMINATED CAPILLARY ARRAY ASSEMBLY

(75) Inventors: Bruce S. Amrhein, Los Alamitos, CA (US); Timothy R. Evans, Whittier, CA (US); Clayton R. Platt, Lake Forest, CA (US); Barry K. Hanamoto, La Mirada, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 221 days.

(21) Appl. No.: 09/607,224

(22) Filed: Jun. 30, 2000

(51) Int. Cl.[7] .............................. C02F 1/40; C02F 11/00; C25B 11/00; C25B 13/00; C25B 9/00; G01N 27/27; G01N 27/403; G01N 27/453

(52) U.S. Cl. ...................... 204/601; 156/300; 156/301; 156/299

(58) Field of Search .................... 204/601; 156/300, 156/301, 299

(56) References Cited

U.S. PATENT DOCUMENTS

| 4,698,123 A | * | 10/1987 | Link et al. ................. 216/24 |
| 5,540,464 A | * | 7/1996 | Picha ..................... 210/198.2 |
| 5,584,982 A | | 12/1996 | Dovichi et al. |
| 5,605,666 A | * | 2/1997 | Goodale et al. ............. 204/452 |
| 5,730,850 A | | 3/1998 | Kambara et al. |
| 6,054,032 A | * | 4/2000 | Haddad et al. ............. 204/451 |
| 6,063,251 A | * | 5/2000 | Kane et al. ............... 204/601 |
| 6,402,875 B1 | * | 6/2002 | Luhmann et al. ........... 156/229 |

OTHER PUBLICATIONS

Richard A. Mathies, et al., "Capillary Array Electrophoresis: An Approach to High–Speed, High–Throughput DNA Sequencing," Nature, vol. 359, pp. 167–169, Sep. 10, 1992.
Hideki Kambara, et al., "Multiple–Sheathflow Capillary Array DNA Analyser," Nature, vol. 361, pp. 565–566, Feb. 11, 1993.

* cited by examiner

*Primary Examiner*—Jill Warden
*Assistant Examiner*—Jennine Brown
(74) *Attorney, Agent, or Firm*—Hogan & Hartson LLP; William H. May; D. David Hill

(57) ABSTRACT

A laminated capillary array assembly having a plurality of capillaries substantially entirely enclosed by a first and a second substrate laminated together. Also disclosed is a capillary array electrophoresis system including the above capillary assembly attached to a sample intake block and an array fitting. Also described is a method for making a laminated capillary array assembly by placing a first substrate on a template having a desired shape, arranging capillaries on the first substrate, and laminating a second substrate on the first substrate to enclose the capillaries between the substrates.

10 Claims, 2 Drawing Sheets

LAMINATED CAPILLARY ARRAY ASSEMBLY

BACKGROUND OF THE INVENTION

1. Area of the Art

This invention relates to a capillary array electrophoresis system and, in particular, to an electrophoresis system with a laminated capillary array assembly.

2. Description of the Prior Art

Electrophoresis has become an indispensable tool of biotechnology, as it is used extensively in a variety of applications, including separation, identification and preparation of pure samples of nucleic acids, proteins and carbohydrates. Traditionally, slab gel electrophoresis has been utilized for DNA sequencing as well as DNA fragment analysis. Recently, capillary gel electrophoresis (CE) has emerged as an attractive alternative to the traditional slab gel method. In CE, an appropriate solution is polymerized or gelled to form a porous matrix in a fused silica capillary tube. An electric field is applied across the matrix. Fragments of sample DNA, injected into one end of the capillary tube, migrate through the matrix under the influence of the electric field at speeds that depend on the length of the fragment. Typically, CE is combined with laser-induced fluorescence (CE-LIF), which provides a high-sensitivity detection. In CE-LIF method, the dideoxynucleotide at one end of a DNA fragment is labeled with a fluorescent marker during a reaction step. When the fragment passes through a beam of light from the laser in the detection zone, the fluorescent marker fluoresces and the fluorescence may be detected. The intensity of the signal depends on the amount of fluorescent marker present in the matrix in the detection zone.

The advantages of CE and CE-LIF arise intrinsically from the use of capillaries with small inner diameters. Since the capillaries have a large surface-to-volume ratio and thin walls, heat generated by Joule heating rapidly dissipates when the capillaries are used in connection with a cooling system. Consequently, high electric fields can be applied along capillaries without a large amount of resistive heating which causes formation of thermal gradients in the gel and impairs separation resolution. Since the electrophoretic velocity of the charged species is proportional to the applied field, CE can achieve rapid, high-resolution separation.

Although the use of CE has greatly improved DNA sequencing rates compared to conventional slab gel electrophoresis, the throughput associated with CE-based DNA sequencing is generally less than that of conventional slab gels when only one capillary is employed in the separation system. In order to overcome this limitation, it has been suggested that a capillary array electrophoresis system, comprising a plurality of spatially organized capillaries, may be used to achieve the desired throughput (*Nature* 359, 167–168, 1992; *Nature* 361, 565–566, 1993). This approach allows independent manipulation of individual capillaries, thereby facilitating rapid, parallel loading and analysis of multiple samples.

Conventionally, in the capillary array electrophoresis system, the capillaries in the array are aligned and irradiated with light. Fluorescence emitted from the fluorophore-tagged DNA or organic compound is detected by scanning a detector relative to the capillaries (U.S. Pat. No. 5,730, 850). Sensitive laser-excited fluorescence detection requires precise alignment of the capillaries in relation to the light source and a photodetector. U.S. Pat. No. 5,730,850 describes stacked capillary array sheets. Each sheet is formed by sandwiching optical-window-facing ends of the capillaries in a capillary holder. The capillary holder is made of a 1.5 mm-thick stainless steel sheet bound to a 0.1 mm-thick polyethylene terephthalate cover. Similarly, in U.S. Pat. No. 5,584,982, the capillaries are closely and evenly spaced, and their end portions are held by a transparent retainer in a fixed position in relation to an optical detection system.

While such capillary holders are useful in retaining one end of the capillaries in a fixed position relative to a light source, they do not protect capillaries from damage caused by their crossing and bending, since large portions of the capillaries are exposed. Bending of the capillaries can result in a loss of the separation efficiency, due to distortions in the gel and multipath effects. Capillary crossover may lead to formation of hot spots. Additionally, mechanical stress, which often leads to capillary breakage, may accumulate at the points where capillaries enter into the capillary holder.

In a typical CE-LIF system, a capillary array is installed in a heater. The heater maintains an elevated temperature along the length of the capillaries to ensure better resolution of DNA fragments. It is, however, difficult to place and retain the capillaries inside the heater. Usually, after installing a capillary array into the heater, a user has to fix each capillary in place with a tape to prevent capillaries from snagging during the operation. Consequently, installation, operation and removal of capillary arrays become laborious. The conventional designs, therefore, fail to provide convenient, stable and sufficiently rigid capillary arrays for CE and CE-LIF.

SUMMARY OF THE INVENTION

Accordingly, the present invention is directed to a laminated capillary array assembly that substantially obviates limitations and disadvantages of the related art.

An object of the present invention is to provide a protection to capillaries forming an array, to prevent their crossover, and to simplify installation and replacement of capillary arrays into a CE instrument.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims hereof as well as the appended drawings.

To achieve these and other advantages, and in accordance with the purpose of the present invention as embodied and broadly described, the present invention provides a capillary assembly comprising a plurality of capillaries substantially entirely enclosed by a first and a second substrate laminated together.

In another aspect, the present invention provides a method for producing a laminated capillary array assembly, comprising the steps of placing a first substrate on a template having a desired shape, arranging capillaries on the first substrate, placing a second substrate on the capillaries, and laminating the first and second substrates together. The capillaries are substantially entirely enclosed between the two substrates, and the laminated capillary assembly of the desired shape is obtained.

The capillary assembly of the present invention is well suited for use in any system that utilizes a plurality of capillaries. Examples of such systems include, but are not limited to CEQ 2000 DNA Analysis System (Beckman Coulter, Inc., Calif.), Amersham Megabase,, and ABI 310, 377 and 3700.

It is to be understood that both the foregoing general description and the following detailed description are exemplary and explanatory and are intended to provide further explanation of the invention as claimed.

BRIEF DESCRIPTION OF THE FIGURES

The above-mentioned and other features of the present invention and the manner of obtaining them will become more apparent, and will be best understood, by reference to the following description, taken in conjunction with the accompanying drawings, in which.

DETAILED DESCRIPTION OF THE EMBODIMENTS OF THE INVENTION

Figure 1:
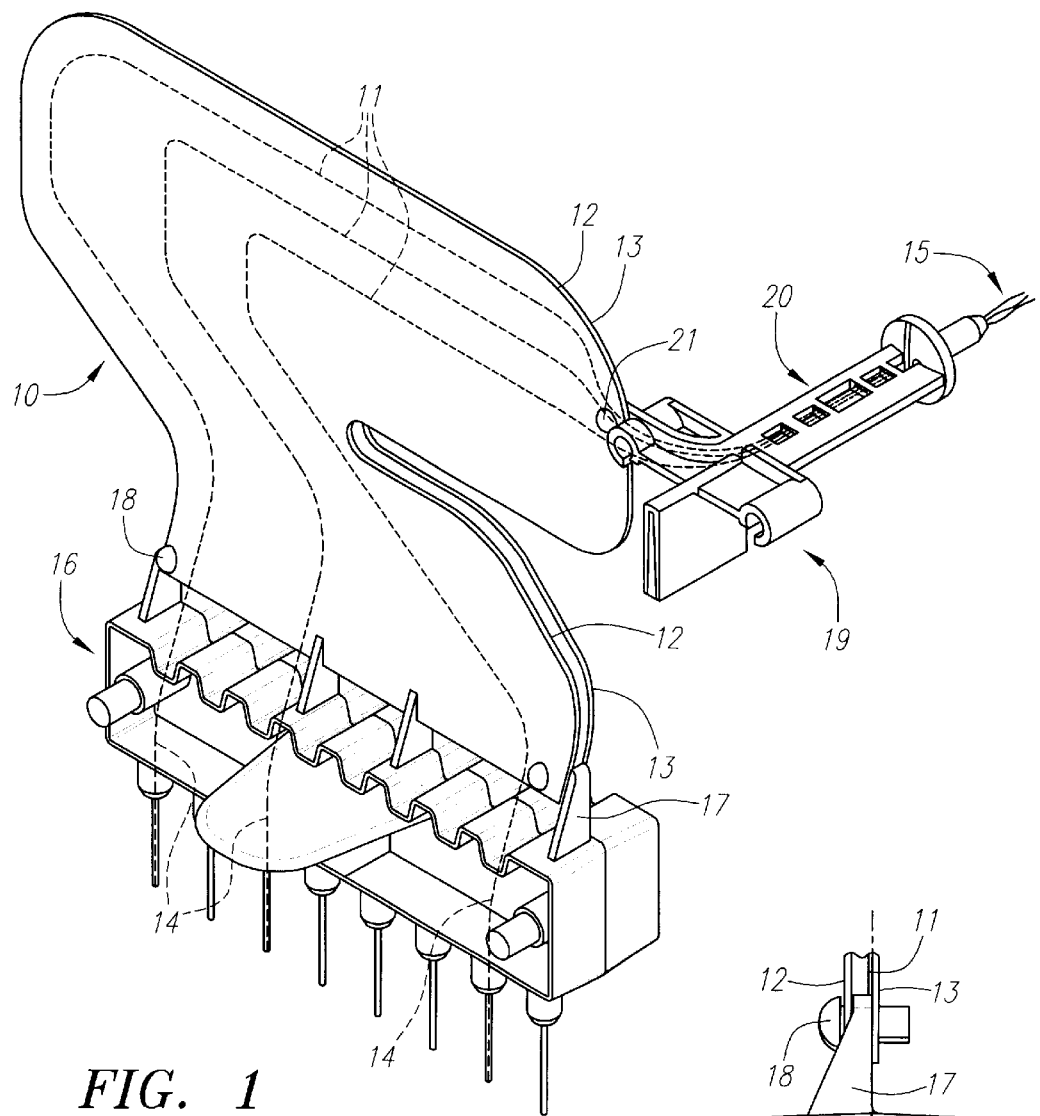
FIG. 1 is a perspective view of a laminated capillary array assembly according to an embodiment of the present invention.
Figure 2:
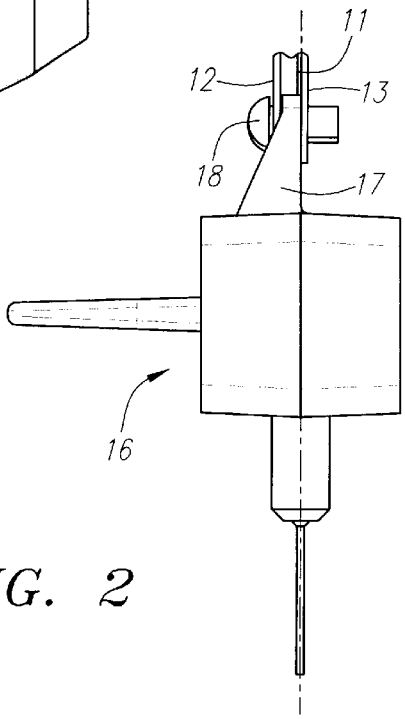
FIG. 2 is a side view of a sample intake block attached to the laminated capillary array assembly of FIG. 1 according to an embodiment of the present invention.

Referring now to FIGS. 1 and 2, a laminated capillary assembly 10 embodying the present invention comprises a plurality of capillaries 11 (only 3 are shown) enclosed by first and second substrates 12 and 13, which are laminated together. Although, the capillary assembly of one embodiment depicted in FIG. 1 includes eight capillaries, a different number of capillaries may be utilized according to this invention. For example, a sixteen-capillary system used in certain CE-LIF applications and characterized by very fine capillaries can be accommodated by this invention.

The capillaries may be fabricated from silica or any other suitable material and have dimensions which may vary with the particular applications. Suitable capillary dimensions include those typically utilized in CE methods, such as lengths of between 20 cm and 500 cm and diameters of between 20 $\mu$m and 500 $\mu$m.

In the capillary assembly of the present invention, the capillaries 11 are substantially entirely enclosed by the first 12 and the second 13 substrate. The capillaries 11 are substantially entirely enclosed when only small portions of capillary ends required for connection with other functional blocks of a CE-LIF instrument are not enclosed by the laminated substrates. The capillaries are considered to be enclosed as long as the laminated substrates restrict lateral movement of the capillaries and prevent their mechanical damage. Consequently, the capillary assembly effectively prevents undesirable bending and breaking of capillaries and simplifies installation and replacement of the capillary arrays.

Any suitable spatial arrangement of the capillaries may be used. Preferably, the capillaries do not cross each other, in order to prevent formation of hot spots. In the embodiment shown in FIG. 1, the capillaries are coplanar, are positioned in a side-by-side arrangement and evenly spaced from each other.

The first and the second substrate may be made of any suitable material, such as plastic films. In one embodiment, the capillary array assembly is made of a material that becomes sufficiently rigid after lamination and retains its shape without any support structures. Examples of such materials include, but are not limited to kapton film, polyester film, and GE Velox. For the purpose of the present invention, the two substrates may be laminated together by any suitable laminating method, such as bonding with an adhesive, melt bonding and ultrasonic welding. In one embodiment, at least one substrate has an adhesive, such as pressure-sensitive adhesive (PSA), applied to its capillary-facing surface. Examples of PSA include, but are not limited to, acrylic-based adhesives such as 3M 468MP and F9473PC, and silicone-based adhesives. Alternatively, an adhesive may be applied to both substrates. The substrates are pressed together to bind and to enclose the capillary array therebetween. A permanent or a releasable adhesive may be used. The releasable adhesive allows for repeated peeling of substrates from each other and rejoining them. In another embodiment, the substrates are heat-treated so that they soften and bind together. As a result the capillary array becomes enclosed therebetween.

Figure 3:
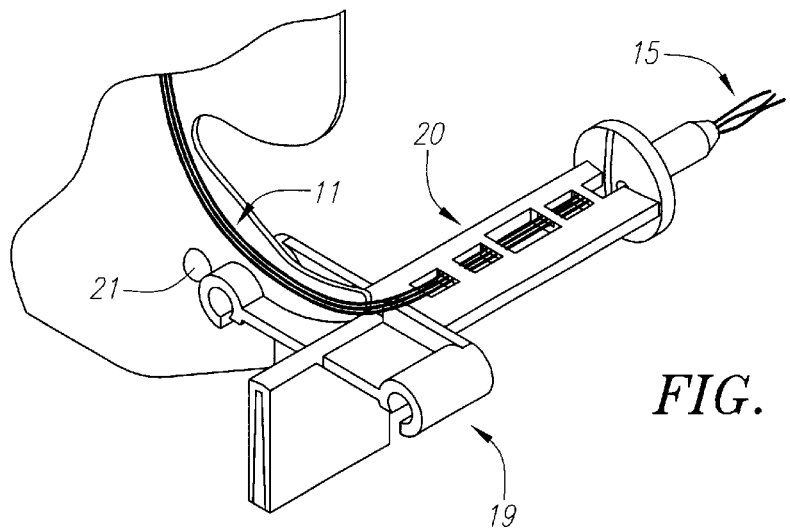
FIG. 3 is a perspective view of an array fitting with a fastener attached to the laminated capillary array assembly of FIG. 1.

Another aspect of this invention provides a capillary array electrophoresis system including, as illustrated in FIGS. 1–3, a laminated capillary array assembly 10 with capillaries 11 having sample intake ends 14 and sample output ends 15 and a controlled temperature chamber (not shown). The temperature chamber typically has a predetermined shape. In a preferred embodiment, the capillary array assembly conforms to the shape of the chamber and closely fits therein.

Referring to FIGS. 1 and 2, the capillary array electrophoresis system embodying the present invention may further comprise a sample intake block 16 for mounting the sample intake ends 14. The sample intake block 16 has a raised flange 17 for anchoring the laminated capillary array assembly 10. The laminated capillary array assembly 10 can be attached to the flange 17 in different ways. In one embodiment, the capillary array assembly 10 is attached to the flange 17 by adhering an already laminated capillary array assembly to the flange. In another embodiment, the flange 17 is sandwiched between the two substrates of the capillary assembly. In this arrangement, at least one substrate is adhered to the flange. Alternatively, the flange 17 of the sample intake block may have at least one mating hole and the capillary assembly 10 may have at least one fastener 18. A particular type of the fastener 18 is not crucial, as long as it securely attaches the capillary assembly to the flange. Examples of fasteners include, but are not limited to, rivets, ties, bolts, and screws. The laminated capillary assembly is anchored to the flange by passing the fastener through the mating hole. When a bolt, screw, or a similar fastener is used, a nut may be required for securing the fastener in place.

Referring to FIGS. 1 and 3, the capillary array electrophoresis system embodying the present invention may further comprise an array fitting 19 for affixing the sample output ends 15 of the capillaries 11 and the optical viewing window 20. The capillary assembly 10 may be anchored to the array fitting 18 with a fastener 21 such as a plastic rivet, screw or snap retainer. A particular type of the fastener 21 is not crucial, as long as it securely attaches the capillary assembly to the array fitting 19.

Figure 4:
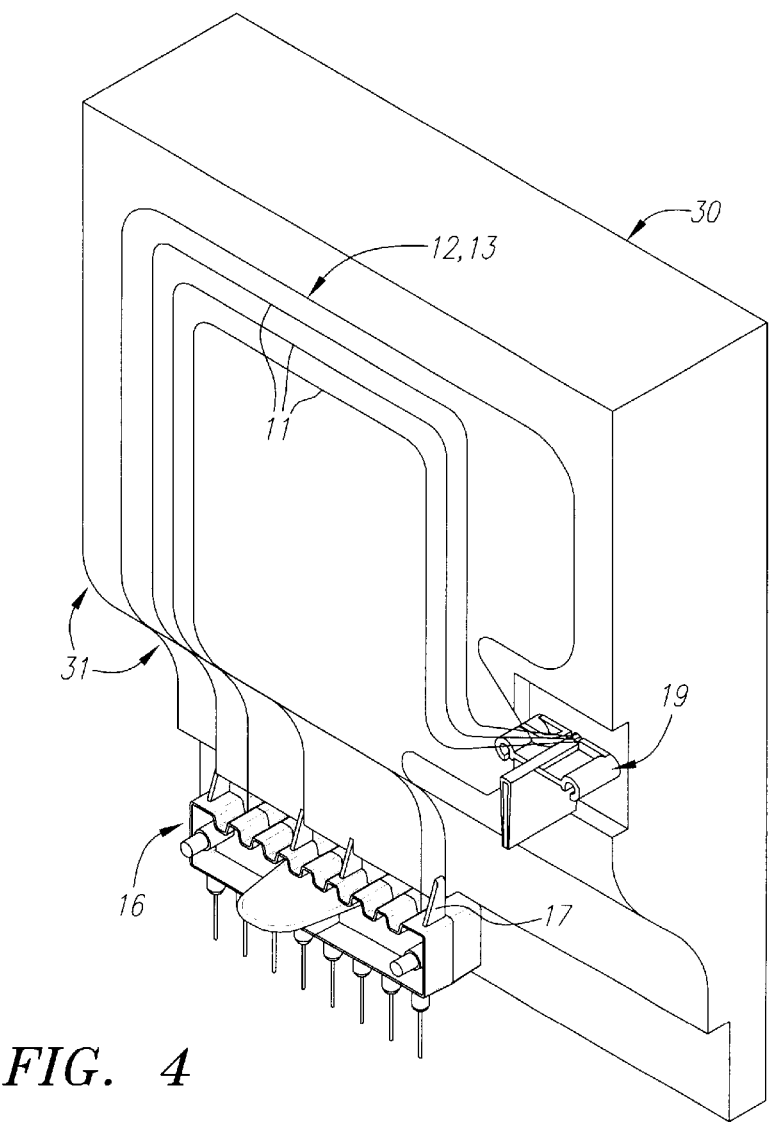
FIG. 4 illustrates forming the laminated capillary array assembly of FIG. 1 on a template according to another embodiment of the present invention.

The present invention also provides a method for making a laminated capillary array assembly. In this method, as illustrated in FIG. 4, a first substrate 12 is placed on a template 30 having a surface 31 of a desired shape. The capillaries 11 are arranged on the first substrate, and a second substrate is placed on the first substrate, covering the capillaries. The first and the second substrate are laminated together, whereby the capillaries are substantially enclosed between the substrates and the laminated capillary assembly of the desired shape is obtained. This method can be used to form capillary assemblies of any desired shape to suit particular applications. The capillaries may be filled with a sample migration medium before or after forming the assembly.

This invention further provides a method of making a capillary array electrophoresis system. This method includes, in addition to the foregoing steps of making a laminated capillary array assembly 10, a step of subsequently attaching the capillary array assembly to a sample intake block 16. In one embodiment the sample intake block 16 has a raised flange 17, and the assembly 10 is anchored to the flange. This step may be carried out in different ways. An additional amount of PSA may be placed on an external surface of one of the substrates after laminating. Then, the assembly can be adhered to a side of the flange 17. In a different embodiment, the capillary array is laminated by adhesion of the first and second substrates. Then, a portion of the laminated substrates is separated, the flange 17 is inserted therebetween, and the substrates are repositioned on the flange. At least one substrate is then attached to the flange by the pressure-sensitive adhesive located on its capillary-facing surface. In another embodiment, the flange 17 is adhered between the substrates during the lamination step. The sample intake block 16 is retained on the template 30 in such a way that its flange 17 meets the sample intake ends 14 of the capillaries 11 and is positioned between the first and second substrates. Consequently, the flange 17 becomes laminated between the first and second substrates.

It will be apparent to those skilled in the art that various modifications and variations can be made in a laminated capillary assembly, and in a method of making a capillary array electrophoresis system with the laminated capillary assembly of the present invention, without departing from the spirit or scope of the inventions. Thus, it is intended that the present invention cover modifications and variations of this invention that come within the scope of the appended claims and their equivalents.

What is claimed is:

1. A capillary array electrophoresis system comprising the laminated capillary assembly comprising a plurality of capillaries substantially entirely enclosed between a first and a second substrate laminated together, wherein the capillary assembly is sufficiently rigid to retain its shape without a support structure and a controlled temperature chamber, wherein the laminated capillary assembly conforms to a shape of the chamber and closely fits into the chamber.

2. A capillary array electrophoresis system comprising (a) the laminated capillary assembly of claim 1, wherein the capillaries have sample intake ends and sample output ends; and (b) a sample intake block for mounting the sample intake ends of the capillaries, wherein the laminated capillary assembly is anchored to the sample intake block.

3. The capillary array electrophoresis system of claim 2, wherein the sample intake block has a raised flange and the capillary assembly is anchored to the flange.

4. The capillary array electrophoresis system of claim 3, wherein an external surface of the laminated capillary assembly is adhered to a side of the flange of the sample intake block by a adhesive.

5. The capillary array electrophoresis system of claim 4, wherein the adhesive is a pressure-sensitive adhesive.

6. The capillary array electrophoresis system of claim 3, wherein the flange of the sample intake block is sandwiched between the first and second substrates of the capillary assembly and wherein at least one substrate is attached to the flange by the pressure-sensitive adhesive plied to the capillary-facing surface of the substrate.

7. The capillary array electrophoresis system of claim 3, wherein the flange of the sample intake block has at least one mating hole and the capillary assembly has at least one fastener, and the capillary assembly is anchored to the flange by the fastener passed through the mating hole.

8. A capillary array electrophoresis system comprising the laminated capillary assembly comprising a plurality of capillaries substantially entirely enclosed between a first and a second substrate laminated together, wherein the capillary assembly is sufficiently rigid to retain its shape without a support structure wherein the capillaries have sample intake ends and sample output ends, and an array fitting for fitting the sample output ends of the capillaries through a pressure and liquid seal, into an optical cell, wherein the capillary assembly is anchored to the array fitting.

9. The capillary array electrophoresis system of claim 8, wherein the capillary assembly is anchored to the array fitting by a fastener.

10. A capillary array electrophoresis system, comprising:
a laminated capillary assembly comprising capillaries with sample intake ends and sample output ends, wherein the capillary assembly is sufficiently rigid to retain its shape without a support structure;
a sample intake block for mounting the sample intake ends of the capillaries, wherein the sample intake block has a flange; and
an array fitting for fitting the sample output ends of the capillaries into an optical viewing window, wherein the array fitting has a fastener,
and wherein the laminated capillary assembly is adhered to the flange with a pressure-sensitive adhesive and is attached to the array fitting by the fastener.

* * * * *